(12) United States Patent
van der Meij et al.

(10) Patent No.: US 6,365,743 B1
(45) Date of Patent: *Apr. 2, 2002

(54) PROCESS FOR THE PREPARATION OF ENANTIOMERICALLY PURE IMIDAZOLYL COMPOUNDS

(75) Inventors: Paulus F.C. van der Meij; Jan-Maarten Verbeek, both of Weesp (NL)

(73) Assignee: Duphar International Research B.V., Weesp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/639,773

(22) Filed: Aug. 16, 2000

Related U.S. Application Data (60) Continuation-in-part of application No. 08/874,454, filed on Jun. 16, 1997, now abandoned, which is a division of application No. 08/728,794, filed on Oct. 10, 1996, now Pat. No. 5,663,343.

(30) Foreign Application Priority Data

Oct. 13, 1995 (EP) .............................. 95202765

(51) Int. Cl.⁷ ...................... C07D 221/18; C07D 233/54
(52) U.S. Cl. ...................... 546/72; 548/311.4; 548/534
(58) Field of Search .................. 546/72; 548/311.4, 548/534

(56) References Cited

U.S. PATENT DOCUMENTS

| | | | |
|---|---|---|---|
| 4,036,852 A | | 7/1977 | Boesten |
| 4,695,578 A | * | 9/1987 | Coates ........................ 514/397 |
| 4,859,662 A | * | 8/1989 | Coates ........................ 514/212 |
| 4,939,136 A | * | 7/1990 | Haeck ........................ 514/183 |

FOREIGN PATENT DOCUMENTS

| | | |
|---|---|---|
| DE | 4238553 | 5/1994 |
| EP | 88201253.7 | 6/1988 |
| EP | 297651 | 1/1989 |
| EP | 375045 | 6/1990 |
| EP | 9311867.1 | 11/1993 |
| EP | DIR 0537 P | 4/1996 |
| GB | 2 153 821 A | 1/1985 |
| NL | 190373 | 1/1985 |

OTHER PUBLICATIONS

J. Chromatogr., Biomed. Appl. 1993, 622/2/, 291–5 /Coll. Pharm., Univ. Georgia, Athens, GA 30602–2352 USA/./ C.A. 120 124005 w/.
Okdada, Tadashi, et al. "Optical resolution of DL–phenylalanine esters." *Chemical Abstracts*, Vol. 78, 1973, p. 556.
Fox, David N., et al. "Optically Active Compounds," *Ullmann's Encyclopedia of Industrial Chemistry*, Vol. A18, 1991, pp. 177–183.
"Chemical Separation of Enantiomers via Diastereomers, ", pp. 324–325.

* cited by examiner

Primary Examiner—Evelyn Mei Huang
(74) *Attorney, Agent, or Firm*—Stevens, Davis, Miller & Mosher, L.L.P.

(57) ABSTRACT

The invention relates to a method for the preparation of an enantiomerically pure imidazolyl compound of the general formula

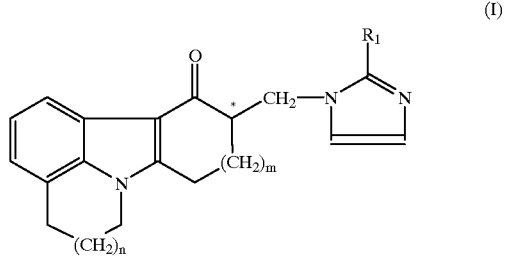

(I)

wherein:
  n is 0 or 1;
  m is 1 or 2;
  $R_1$ is hydrogen, methyl or ethyl; and
  C* denotes a chiral center;
as well as its pharmaceutically acceptable acid addition salt.

The invention further relates to a method of racemization and to a new acid addition salt of this formula I compound and D-pyroglutamic acid and to the hydrochloride monohydrate of the compound of formula I.

24 Claims, 2 Drawing Sheets

PROCESS FOR THE PREPARATION OF ENANTIOMERICALLY PURE IMIDAZOLYL COMPOUNDS

CROSS-REFERENCE TO RELATED APPLICATIONS

This application is a continuation-in-part application of U.S. Ser. No. 08/874,454, filed Jun. 16, 1997, abandoned, which is a divisional application of U.S. Ser. No. 08/728,794, filed Oct. 10, 1996, now U.S. Pat. No. 5,663,343.

The present invention relates to a process for the preparation of an enantiomerically pure imidazolyl compound, as well as to an acid addition salt of this compound.

4,5,6,8,9,10-Hexahydro-10-[(2-methyl-1H-imidazol-1-yl)methyl-11H-pyrido[3,2,1-jk]carbazol-11-one is known from EP-B-0297651 and from EP-A-0601345. In the former patent publication a general class of compounds, including the above imidazolyl compound and homologous compounds, their preparation and their use as 5-HT antagonists is described. The latter patent publication describes the use of a selection of these type of compounds for the treatment of certain diseases.

Various biologically active substances that are used in pharmaceutical compositions for human or veterinary application, contain a chiral centre in their molecular structure and therefore give rise to optical isomerism. It is generally known in the art, that often only one of the enantiomers presents the desired optimum biological activity. The presence of the other optical antipode in a composition or agent may cause or invigorate certain side effects and burden the recipient, i.c. the human or animal body. It is generally deemed more and more desirable to administer the biologically active substance in the form of a substantially pure enantiomer, which specifically exhibits the desired biological activity. Therefore, the resolution of a racemate into its enantiomers is often an important step in the preparation process of pharmacologically active substances.

It has been found, that the R-(-)-enantiomer of the above-defined imidazolyl compound, also known under its generic name cilansetron, is especially useful in the indications mentioned in EP-A-0601345. It is therefore desirable to dispose of a method for the separation of the R-enantiomer from the racemate.

There are essentially three methods available to resolve racemates into their respective enantiomers. The first of these, viz. a resolution based on difference in physical properties, e.g. in crystal structure, is only occasionally applicable.

In a more recent method of resolution, enzymes are applied to chemically modify one enantiomer of a racemate selectively, followed by a separation of the modified from the unmodified enantiomer.

The third and by far most generally used method of resolution involves a reaction with a—commercially available—optically active reagent to produce diastereomers, which differ in physical properties. So, the diastereomers obtained in this manner can be separated, e.g. by crystallization, after which the desired enantiomer can be isolated by a chemical after-treatment.

It is generally known in the art that the resolution of enantiomers by preparing diastereomers is a very difficult task. Even experienced investigators find that certain compounds resist chemical resolution by any one of a number of combinations of resolving agents and reaction conditions.

As a general rule, investigators in the art of separating enantiomers commence a study by using reagents and conditions that have been found to be successful in the past in resolving similar compounds. A generally preferred method for resolving racemates of the above imidazolyl compounds is a reaction with an optically active acid, after which the diastereomers obtained can be separated, preferably by crystallization. In EP 0297651 the use of (+)-di-O,O'-p-toluyl-D-tartaric acid is described. Apparently this optically active carboxylic acid is the reagent of choice for resolving such racemates, because the same acid has also been used for the resolution of a chemically closely related imidazolyl compound, viz. 1,2,3,9-tetrahydro-9-methyl-3-[(2-methyl-1H-imidazol-1-yl)methyl]-4H-carbazol-4-one or ondansetron (e.g. NL-B-190373, Example XX). This is indeed remarkable in view of the fact that the resolution with (+)-di-O,O'-p-toluyl-D-tartaric acid has various disadvantages, such as the use of a high dilution and the application of a less acceptable solvent system, viz. DMF-water. Such a diluted solution is not attractive or even not feasible from an economical point of view. Furthermore, the solvent DMF has well-known disadvantages, such as a high boiling point and a considerable toxicity (suspected carcinogenity).

In addition to the above optically active di-O,O'-p-toluyl-D-tartaric acid, a number of chiral dicarbonic acids, chiral sulfonic acids or chiral monocarbonic acids are commercially available, such as dibenzoyl-L-tartaric acid, L-tartaric acid, L-malic acid, D-camphor-10-sulfonic acid, D-quinic acid, 2,3:4,6-di-O-isopropylidene-2-keto-L-gulonic acid, L-mandelic acid, R-2-(4-hydroxyphenoxy)propionic acid, and (-)-1,3,2-dioxa-phosphorinane-5,5-dimethyl-2-hydroxy-4-phenyl-2-oxide. As will become apparent from the Examples, however, these acids either do not effect a precipitation of the addition salt with one of the enantiomers, or do not accomplish enrichment of one of the enantiomers in the precipitate.

It is the objective of the present invention to provide an economically operative method for the preparation of enantiomerically pure imidazolyl compounds, which method should meet the following requirements: (a) using non-diluted reaction conditions and an acceptable solvent, (b) easy recycling of the relatively expensive chiral acid.

This objective can be achieved by a method for the preparation of an enantiomerically pure imidazolyl compound of the general formula (I)

wherein:
  n is 0 or 1;
  m is 1 or 2;
  $R_1$ is hydrogen, methyl or ethyl; and
  C* denotes a chiral centre;
as well as its pharmaceutically acceptable acid addition salt;
  a) by adding a carboxylic acid in an optically active form to a solution of a racemic mixture of the above compound I, followed by separation of the crystallized acid addition salt of said mixture of enantiomers of compound I enriched in one enantiomer, from the mother liquor enriched in the other enantiomer, b) when the crystallized acid addition salt is enriched in the undesired enantiomer, by then separating the mixture of enantiomers in the mother liquor from said optically active carboxylic acid, followed by addition of a racemic mixture of said carboxylic acid to a solution of the obtained mixture of isomers of I, and by separation of the crystallized acid addition salt of said mixture, enriched in the desired enantiomer, from the mother liquor, and (c) optionally recrystallizing the product until the desired enantiomeric purity is obtained, and by then (d) converting this acid-addition salt of the desired enantiomer to the desired enantiomerically pure imidazolyl compound of the general formula I or to its pharmaceutically acceptable acid addition salt, characterized in that pyroglutamic acid is used as said carboxylic acid.

When the acid addition salt formed is enriched in the desired enantiomer it can be isolated and, as soon as it has the desired enantiomeric purity by further treatment, be converted into the desired enantiomerically pure imidazole compound or its pharmaceutically acceptable acid addition salt. For the sake of convenience such a direct crystallization of the desired enantiomer is preferred. When the acid addition salt formed upon addition of the optically active pyroglutamic acid is enriched in the undesired enantiomer the mutual resolution approach (Eliel, E. L., Wilen, S. H and Mander, L. N. in Stereochemistry or Organic Compounds, John Wiley & Sons, Inc., New York (1994), 325)is used. In this approach, after the first resolution step yielding the acid addition salt enriched in the undesired enantiomer, the optically active pyroglutamic acid is removed from the dry substance obtained from the mother liquor, e.g. by a solvent extraction in a dichloromethane/water system. Subsequently the second step is performed by adding racemic pyroglutamic acid to a solution of the mixture of isomers of I obtained, leading to the crystallization of the acid addition salt of the desired enantiomer.

In view of the finding (see the Examples), that the chemically closely related imidazolyl compound ondansetron cannot be resolved in its optical antipodes with the use of optically active pyroglutamic acid, it is quite a surprise, that the above desired enantiomer of the general formula I can so easily be obtained by using pyroglutamic acid in an optically active form, optionally followed by addition of the racemic pyroglutamic acid, while meeting the above-defined requirements. It is further beyond expectation, that pyroglutamic acid has a so favourable effect on the resolution of a racemate of the formula I imidazolyl compound, in view of the poor results obtained with a large series of other resolving agents.

The enantiomerically pure imidazolyl compound according to the present invention should be understood to encompass optically active compounds having an enantiomeric excess (e.e.) of over 90%. The crystalline acid addition salt of the desired enantiomerically pure imidazolyl compound obtained can be converted to the pure enantiomer as such by methods which are well-known in the art of salt-cleavage. Generally a cleavage under the influence of a base can be used, upon which the desired free enantiomerically pure imidazolyl base is formed. If desired, said imidazolyl base can be converted to a pharmaceutically acceptable acid addition salt by treating it with an acid such as HCl, maleic acid and other suitable acids as defined in EP-A-601345.

Figure 1:
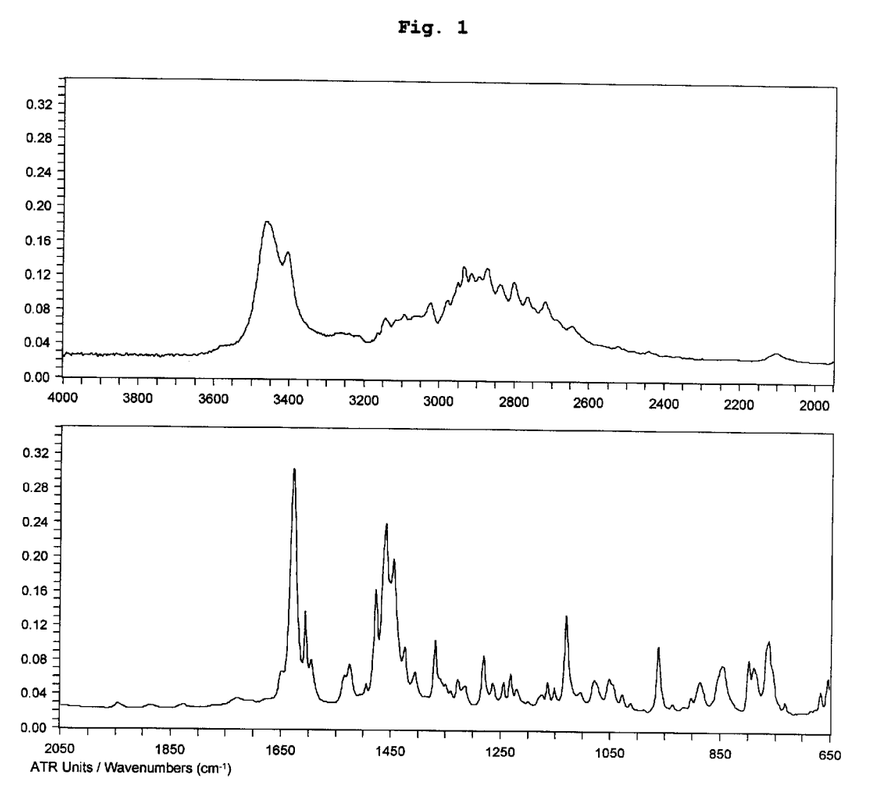
FIG. 1 IR spectrum of cilansetron hydrochloride monohydrate ν(X-H) stretching region (top) and fingerprint region (bottom).

The present invention relates more in particular to a method for the preparation of cilansetron, i.e. of an enantiomerically pure imidazolyl compound of the general formula I, wherein m and n are both 1, $R_1$ is methyl and the C* atom has the R-configuration. In a preferred embodiment the present invention relates to the preparation of crystalline cilansetron hydrochloride monohydrate, in particular in the so-called crystalline modification A, which is a stable and non-hygroscopic form of cilansetron with advantageous properties in the art of pharmaceutical formulations. Therefore the present invention also relates to a new compound, i.e. crystalline cilansetron hydrochloride monohydrate, in particular in the so-called crystal modification A. The cilansetron hydrochloride monohydrate of the present invention may be well characterized by spectroscopic data, e.g. by Infrared (=IR) spectrum, e.g. by the most relevant ν (X-H) stretching vibration frequency region, or by powder X-ray diffraction (=XRD) pattern. The Fourier transform IR spectrum for the cilansetron hydrochloride monohydrate of the present invention is shown in FIG. 1, and the powder X-ray diffraction (=XRD) pattern in FIG. 2, respectively.

The crystallization procedure, i.e. the separation of the crystallized acid addition salt of the desired enantiomer or, at least, of the racemate enriched in the desired enantiomer, is preferably performed in an alcoholic solvent. Suitable examples of alcoholic solvents for this crystallization process are methanol, ethanol, isopropanol and butanol. The final crystallization step is preferably carried out in isopropanol or n-butanol. When the final crystallization for cilansetron is carried out in water and hydrochloric acid containing alcoholic solvent, preferably in isopropanol or butanol, the compound crystallizes as the hydrochloride monohydrate in the stable crystal modification A. In the process of the invention, the optically active acid used, viz. D-pyroglutamic acid [R-2-pyrrolidone-5-carboxylic acid] in the direct approach and L-pyroglutamic acid [S-2-pyrrolidone-5-carboxylic acid] in the mutual resolution approach for the resolution of cilansetron, is preferably added in an amount of between 0.2 and 1.5 equivalent, calculated on the starting racemic mixture.

The ratio of the solvent volume to the amount of enantiomers in the mixture being resolved can be varied over a relatively broad range. In the direct approach the ratio of the amount of solvent to the amount of enantiomers can typically be about 3:1 to 15:1, where the ratio is expressed as the volume of solvent relative to the weight of the enantiomers in the solvent. Preferably the ratio is about 5:1 to about 10:1. In a preferred embodiment the ratio of the volume of solvent to the weight of enantiomers is about 7:1. In the mutual resolution approach the ratio of the amount of solvent to the amount of enantiomers can typically be about 3:1 to 15:1 in the first step and 5:1 to 15:1 in the second step. Preferably the ratio is about 5:1 to about 10:1 in the first step and 7:1 to 12:1 in the second step. In a preferred embodiment the ratio of the volume of solvent to the weight of enantiomers is about 7:1 in the first step and 10:1 in the second step.

The solution containing the enantiomers can be prepared by dissolving the enantiomeric mixture in the solvent. Dissolution can typically be carried out at a temperature of about 25° C. to about 80° C., but will generally be carried out at a temperature of about 50° C. to about 60° C. The crystallization can typically be carried out at a temperature of about −20° C. to +20° C., but will generally be carried out at a temperature of about −10° C. to about 0° C.

It remains unsatisfactory, however, that the yield of the desired enantiomer is theoretically below 50%, based on starting racemate. As an additional feature of the present invention it has now been found, that the mother liquor or combined mother liquors, remaining after the crystallization procedure, can be subjected to an after-treatment comprising a racemization step, to allow an overall yield of the desired enantiomer of over 50% after the subsequent crystallization procedure as described above.

Consequently, the present invention also relates to a method as defined hereinbefore, which method is characterized in that the mother liquor or combined mother liquors, remaining after the separation of the crystallized acid addition salt, is (are) subjected to an after-treatment by successively (i) cleaving the dissolved acid addition salt to produce a solution of an enantiomers-mixture of the imidazolyl compound of the general formula I, presented above, which mixture has a reduced content of the desired enantiomer, and (ii) by then converting said solution to a racemic mixture under the influence of a base. In the case of the mutual resolution approach, the acid addition salt enriched in the undesired enantiomer can optionally be added to the (combined) mother liquor(s). Preferably an inorganic base, such as an alkali metal hydroxide, is used for the racemization.

After the above-described racemization, the recovered racemate can be subjected again to the above crystallization procedure, using optically active pyroglutamic acid, optionally followed by racemic pyroglutamic acid, to yield another crop of enantiomerically pure imidazolyl compound. If desired, the (combined) mother liquor(s) from this latter crystallization procedure can be racemized again, etc., etc. In this manner, the total yield of the combined crop of the desired enantiomer can be increased considerably. In a technically and economically attractive realization, the recovered racemate can be added to the starting racemate for the next batch, so that in the overall reaction procedure substantially no material will be lost.

The acid addition salt of an enantiomerically pure imidazolyl compound of the general formula I, in particular of cilansetron, and D-pyroglutamic acid is new. Therefore the present invention also relates to this acid addition salt which can be obtained by the crystallization process as described hereinbefore.

The invention will be described in more detail with reference to the following specific Examples.

EXAMPLE I

Preparation of (R)-(−)-4,5,6,8,9,10-hexahydro-10-
[(2-methyl-1H-imidazol-1-yl)methyl]-11H-pyrido-
[3,2,1-jk]-carbazol-11-one hydrochloride
monohydrate (cilansetron) By Direct Resolution in
Methanol Followed By Crystallisation from
Isopropanol 25.00 g of (R,S)-4,5,6,8,9,10-hexahydro-10-[(2-methyl-1H-imidazol-1-yl)methyl]-11H-pyrido-[3,2,1-jk]-carbazol-11-one and 10.11 g of R-2-pyrrolidone-5-carboxylic acid (D-pyroglutamic acid) in 175 ml of methanol are heated to 50° C. The so formed suspension of the diastereomeric salts is stirred for 1 hour at that temperature. The mixture is cooled to 0° C. and stirred for 1 hour at that temperature. The solid substance is sucked off, washed with cold methanol and dried. Yield: 25.91 g. This crystallization procedure is repeated twice using 5 ml of methanol per 1 g of the obtained salt for the first repetition and 10 ml of methanol per 1 g of salt for the second repetition. Yield: 11.91 g.

The mother liquors of the three crystallizations are combined and used for the winning of a second crop. 10.00 g of the above obtained salt is stirred during 15 minutes with 200 ml of water, 50 ml of dichloromethane and 6.00 g of sodium bicarbonate. After separation of the two layers, the water layer is extracted twice with 25 ml of dichloromethane. The combined dichloromethane layers are evaporated to dryness.

The so obtained dry substance is dissolved in 60 ml of isopropanol. 2.5 ml of concentrated hydrochloric acid is added to this solution at room temperature. After stirring for 1 hour the formed solid substance is sucked off, washed with cold isopropanol and petroleum ether 40–65 and dried. The yield of the title compound is 7.93 g. (e.e. 94%). Melting point: 219° C. $[\alpha]_D^{25}$=−6.9 (c=1.8; methanol).

EXAMPLE II

Preparation of (R)-(−)-4,5,6,8,9,10-hexahydro-10-
[(2-methyl-1H-imidazol-1-yl)methyl]-11H-pyrido-
[3,2,1-jk]-carbazol-11-one hydrochloride
monohydrate (cilansetron) By Direct Resolution In
and Crystallisation from Butanol To 21.90 kg of (R,S)-4,5,6,8,9,10-hexahydro-10-[(2-methyl-1H-imidazol-1-yl)methyl]-11H-pyrido-[3,2,1-jk]-carbazol-11-one and 8.90 kg of R-2-pyrrolidone-5-carboxylic acid (D-pyroglutamic acid) in 145.5 l of 1-butanol and 14.5 l of water at 60° C. is added 8.90 kg of D-pyoglutamic acid.

The resulting suspension of diastereomeric salts is stirred for 30 minutes at 60° C. Subsequently the suspension is cooled down to 0° C. in about 1 hour, followed by stirring for 1 hour at 0° C. The solid substance is sucked off, washed with cold 1-butanol, followed by washing with tertiair-butyl methyl ether, The solid substance is dried. Yield: 16.4 kg. The crystallization is repeated twice using 10 l of 1-butanol and 1 l of water per kg of salt for the first repetition and 7 l of 1-butanol and 0.7 l of water for the second repetition. Yield: 7.93 kg. The mother liquors of the three crystallizations are combined and used for the winning of a second crop.

7.9 kg of the above obtained salt is stirred for 15 minutes with 2.3 kg of potassium bicarbonate in 47.6 l of 1-butanol and 23.8 l of water. After separation of the two layers, the water layer is extracted with 11.9 l of 1-butanol. The combined 1-butanol layers are washed with 15.9 l of water. 35 l of 1-butanol/water is distilled off at ≦60° C. under reduced pressure. To the resulting solution 1.6 l of hydrochloric acid 36% m/m is added. After stirring for 30 minutes at 0° C. the formed solid substance is sucked off, washed with cold 1-butanol, followed by washing with tertiar-butyl methyl ether. The yield of the title compound is 6.24 kg (e.e. 97%). Melting point: 218° C. $[\alpha]_D^{25}$=−5.2 (c=1.8; methanol).

Spectroscopic Investigation of the Crystalline Product
(a) Infrared (=IR) Spectrum The characteristic IR data (cm$^{-1}$) for the cilansetron hydrochloride monohydrate of the invention was as follows: Infrared (=IR) spectra bands recorded in attenuated total reflectance (=ATR; spectral resolution 2 cm$^{-1}$, deuterated triglycine sulfate detector) in cm$^{-1}$ (maximum confidence interval±2 cm$^{-1}$ with α-level=0.05 at a degree of freedom f=5): 3461, 3405, 2103, 1729, 1649, 1628, 1606, 1460, 1281, 962.

The complete IR spectrum for the cilansetron hydrochloride monohydrate compound of the present invention is shown in FIG. 1.

From the OH bands in the IR spectrum it can be straightforwardly deduced that the cilansetron hydrochloride monohydrate compound of the present invention represents a uniform crystalline monohydrate modification.

(b) Powder X-ray Diffraction Pattern

The powder X-ray diffraction pattern for the cilansetron hydrochloride monohydrate compound of the invention powder X-ray diffraction (=XRD) pattern was measured on diffractometer using monochromatic CuKα radiation, tube voltage 40 kV, tube current 40 mA, resulting in the following powder X-ray diffraction (=XRD) angles (2 theta; maximum confidence interval±0.1° with α-level=0.05 at a degree of freedom f=5): 5.7°±0.1°, 10.8°±0.1°, 11.4°±0.1°, 12.4°±0.1°, 17.2°±0.1°, 22.7°±0.1° (degree of freedom f=3), 23.0°±0.1°, 24.5°±0.1°, 27.4°±0.1°, 35.0°±0.1°.

The powder X-ray pattern confirms the above conclusions from the IR spectrum, e.g. in that the cilansetron hydrochloride monohydrate compound may be obtained by the process of the present invention as an essentially pure crystalline modification.

Figure 2:
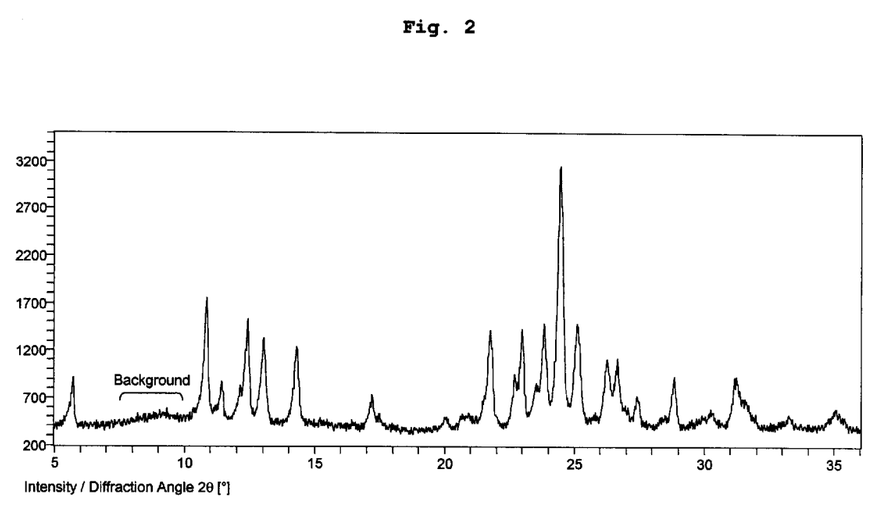
FIG. 2 Powder X-ray diffraction pattern of cilansetron hydrochloride monohydrate.

The complete powder X-ray diffraction pattern for the cilansetron hydrochloride monohydrate compound of the present invention is shown in FIG. 2.

EXAMPLE III

Preparation of (R)-(−)-4,5,6,8,9,10-hexahydro-10-[(2-methyl-1H-imidazol-1-yl)methyl]-11H-pyrido-[3,2,1-jk]-carbazol-11-one hydrochloride monohydrate (cilansetron) By Mutual Resolution 25.00 g of (R,S)-4,5,6,8,9,10-hexahydro-10-[(2-methyl-1H-imidazol-1-yl)methyl]-11H-pyrido-[3,2,1-jk]-carbazol-11-one and 10.11 g of S-2-pyrrolidone-5-carboxylic acid (L-pyroglutamic acid) in 175 ml of methanol are heated to 50° C. The so formed suspension of the diastereomeric salts is stirred for 1 hour at that temperature.

The mixture is cooled to 0° C. and stirred for 1 hour at that temperature. The solid substance is sucked off, washed with cold methanol and dried. Yield: 18.5 g. The methanol is evaporated from the mother liquor. The residue is stirred during 15 minutes with 200 ml of water, 50 ml of dichloromethane and 6.00 g of sodium bicarbonate. After separation of the two layers, the water layer is extracted twice with 25 ml of dichloromethane. The combined dichloromethane layers are evaporated to dryness. The so obtained dry substance (11.50 g) and 4.75 g of R,S-pyrrolidone-5-carboxylic acid (D,L-pyroglutamic acid)are dissolved in 115 ml of methanol by heating till reflux. The solution is cooled to room temperature and stirred for 1 hour at that temperature. The formed solid substance is sucked off, washed with cold methanol and dried. yield: 6.00 g (e.e. 97%). 5.00 g of the above obtained salt is stirred during 15 minutes with 100 ml of water, 25 ml of dichloromethane and 3.00 g of sodium bicarbonate. After separation of the two layers, the water layer is extracted twice with 12.5 ml of dichloromethane. The combined dichloromethane layers are evaporated to dryness.

The so obtained dry substance is dissolved in 30 ml of isopropanol. 1.25 ml of concentrated hydrochloric acid is added to this solution at room temperature. After stirring for 1 hour the formed solid substance is sucked off, washed with cold isopropanol and petroleum ether 40–65 and dried. The yield of the title compound is 3.95 g (e.e. 98%). Melting point: 219° C.

EXAMPLE IV

Racemization of the Combined Mother Liquors to (R,S)-(−)-4,5,6,8,9,10-hexahydro-10-[(2-methyl-1H-imidazol-1-yl)methyl]-11H-pyrido-[3,2,1-jk]-carbazol-11-one and Winning of a Second Crop of the R-enantiomer By Direct Resolution The methanol is evaporated from the combined mother liquors of example I. The residue is stirred during 15 minutes with 250 ml of water, 100 ml of dichloromethane and 10.00 g of sodium bicarbonate. After separation of the two layers, the water layer is extracted with 50 ml of dichloromethane.

The combined dichloromethane layers are evaporated to dryness. The so obtained dry substance is dissolved in 90 ml of methanol and 20 ml of water. For the racemization 2.0 g of potassium hydroxide, dissolved in 5 ml of water, is added. After stirring for 30 minutes, the reaction mixture is neutralized with 2 N hydrochloric acid. 500 ml of water is added to this solution. The methanol/water layer is extracted with dichloromethane, once with 100 ml and twice with 50 ml. The combined dichloromethane layers are evaporated to dryness.

To the so obtained dry substance, 6.1 g of R-2-pyrrolidone-5-carboxylic acid and 75 ml of methanol are added. The temperature is raised to 50° C. The so formed suspension of diastereomeric salts is stirred for 1 hour at that temperature. The mixture is cooled to 0° C. and stirred for 1 hour at that temperature. The solid substance is sucked off, washed with cold methanol and dried. Yield of addition salt: 7.49 g. This crystallization procedure is repeated twice using 5 ml of methanol per 1 g of the obtained salt for the first repetition and 10 ml of methanol per 1 g of salt for the second repetition. Yield: 4.97 g.

The so obtained salt is stirred during 15 minutes with 100 ml of water, 25 ml of dichloromethane and 3.00 g of sodium bicarbonate. After separation of the two layers, the water layer is extracted twice with 15 ml of dichloromethane. The combined dichloromethane layers are evaporated to dryness. The so obtained dry substance is dissolved in 30 ml of isopropanol. 1.3 ml of concentrated hydrochloric acid is added to this solution at room temperature. After stirring for 1 hour the formed solid substance is sucked off, washed with cold isopropanol and petroleum ether 40–65 and dried.

An additional amount of the title compound is obtained of 3.12 g (e.e. 95%). Melting point: 219° C. In the same way the mother liquors of example II, combined with the acid addition salt enriched in the undesired enantiomer can be racemised and crystallized (by direct approach or mutual resolution approach).

EXAMPLE V

Attempted Resolution of R,S-1,2,3,9-tetrahydro-9-methyl-3-[(2-methyl-1H-imidazol-1-yl)methyl]-4H-carbazol-4-one (Ondansetron)

0.50 g of (R,S)-1,2,3,9-tetrahydro-9-methyl-3-[(2-methyl-1H-imidazol-1-yl)methyl]-4H-carbazol-4-one and 0.22 g of R-2-pyrrolidone-5-carboxylic acid in 5.0 ml of methanol are heated to 50° C. The so formed clear solution is cooled to 0° C. in 30 minutes. After stirring for 1 hour at 0° C. the formed crystals are sucked off, washed with cold methanol and dried. Yield: 0.02 g. According to HPLC the R/S ratio is 1:1. This means that no enrichment has occurred. This experiment is repeated on the same scale, but instead of 5.0 ml of methanol 1.5 ml is used. Yield: 0.12 g. The R/S ratio is also 1:1.

EXAMPLE VI

Comparative Experiments

In a corresponding manner as described in Example I, the separation of cilansetron from the racemate is investigated with the use of a number of commercially available optically active acids. The results obtained are tabulated below. From these results the following conclusion can be drawn:

Conclusion

Only upon use of D-pyroglutamic acid (R-2-pyrrolidone-5-carboxylic acid) the desired enrichment in the R-enantiomer is obtained.

| Acid | 96% Ethanol | 100% Ethanol | 100% Methanol | Water |
|---|---|---|---|---|
| Di-O,O'-p-toluyl-D-tartaric acid | ↓, R = S | ↓, R < S | ↓, R < S | — |
| Di-O,O'-p-toluyl-L-tartaric acid | — | — | ↓, R > S | — |
| Dibenzoyl-L-tartaric acid monohydrate | — | — | ↓, R < S | — |
| L-Tartaric acid | ↓, R = S | ↓, R = S | — | — |
| L-Malic acid | — | ↓, R = S | — | — |
| D-Camphor-10-sulfonic acid monohydrate | X | ↓, R = S | X | X |
| D-Quinic acid | X | X | X | X |
| 2,3:4,6-Di-O-isopropyledene-2-keto-L-gulonic acid | X | X | X | X |
| L-Mandelic acid | — | X | — | X |
| (R)-2-(4-Hydroxyphenoxy)propionic acid | X | — | X | — |
| (-)-1,3,2-Dioxa-phosphorinane-5,5-dimethyl-2-hydroxy-4-(phenyl)-2-oxide | X | X | X | X |
| R-2-Pyrrolidone-5-carboxylic acid | ↓, R >> S | ↓, R >> S | ↓, R >> S | — |

—: no experiment performed
X: no precipitation
↓: precipitation
R = S: no enrichment
R > S: R enriched in the crystal; little selectivity (e.e. up to 50%)
R >> S: R enriched in the crystal; good selectivity (e.e. over 50%)
R < S: R enriched in the mother liquor; little selectivity

What is claimed is:

1. Method for the preparation of an enantiomerically pure imidazolyl compound I of the formula wherein:
n is 0 or 1;
m is 1 or 2;
R₁ is hydrogen, methyl or ethyl; and
C* denotes a chiral centre;

as the monohydrate of its hydrochloric acid addition salt;

a) by adding a pyroglutamic acid in an optically active form to a solution of a racemic mixture of the above compound I, followed by separation of the crystallized acid addition salt of said mixture of enantiomers of compound I enriched in one enantiomer, from the mother liquor enriched in the other enantiomer, b) when the crystallized acid addition salt is enriched in the undesired enantiomer, by then separating the mixture of enantiomers in the mother liquor from said acid, followed by addition of a racemic mixture of said acid to a solution of the obtained mixture of isomers of I, and by separation of the crystallized acid solution addition salt of said mixture, enriched in the desired enantiomer, from the mother liquor, and by;

c) optionally recrystallizing the product until the desired enantiomeric purity is obtained, and by then d) converting this acid-addition salt of the desired enantiomer to the desired enantiomerically pure imidazolyl compound I of the formula as its hypochloride monohydrate.

2. Method for the preparation of an enantiomerically pure imidazolyl compound I of the formula wherein:
n is 0 or 1;
m is 1 or 2;
R₁ is hydrogen, methyl or ethyl; and
C* denotes a chiral centre;

as the monohydrate of its hydrochloric acid addition salt;

a) by adding an optially active D-pyroglutamic acid to a solution of a racemic mixture of the above compound I, followed by separation of the crystallized acid addition salt of said mixture enriched in the desired enantiomer, from the mother liquor, and by b) optionally recrystallizing the product until the desired enantiomeric purity is obtained, and by then;

c) converting this acid-addition salt obtained to the desired enantiomerically pure imidazolyl compound I of the formula as its hypochloride monohydrate.

3. Method for the preparation of an enantiomerically pure imidazolyl compound I of the formula wherein:
n is 0 or 1;
m is 1 or 2;
$R_1$ is hydrogen, methyl or ethyl; and
C* denotes a chiral centre;
as the monohydrate of its hydrochloric acid addition salt;
a) by adding an optically active L-pyroglutamic acid to a solution of a racemic mixture of the above compound I, followed by separation of the crystallized acid addition salt of said mixture, enriched in the undesired enantiomer, from the mother liquor, followed by
b) separating the mixture of enantiomers in the mother liquor from said acid, addition of a racemic mixture of said acid separation of the crystallized acid addition salt of said mixture of enantiomers of compound I, enriched in the desired enantiomer, from the mother liquor, and by
c) optionally recrystallizing the product until the desired enantiomeric purity of obtained, and by then
d) converting the acid-addition salt of the desired enantiomer obtained, to the desired enantiomerically pure imidazolyl compound I of the formula I as its hydrochloride monohydrate.

4. Method as claimed in claim 1, wherein a compound of formula I is prepared, wherein:
n is 1;
m is 1;
$R_1$ is methyl; and
the C* atom has the R-configuration.

5. Method as claimed in claim 2, wherein a compound of formula I is prepared, wherein:
n is 1;
m is 1;
$R_1$ is methyl; and
the C* atom has the R-configuration.

6. Method as claimed in claim 3, wherein a compound of formula I is prepared, wherein:
n is 1;
m is 1;
$R_1$ is methyl; and
the C* atom has the R-configuration.

7. Method as claimed in claim 1, wherein pyroglutamic acid in an optically active form is added in an amount of between 0.2 and 1.5 equivalent, calculated on the starting racemic mixture.

8. Method as claimed in claim 2, wherein pyroglutamic acid in an optically active form is added in an amount of between 0.2 and 1.5 equivalent, calculated on the starting racemic mixture.

9. Method as claimed in claim 3, wherein pyroglutamic acid in an optically active form is added in an amount of between 0.2 and 1.5 equivalent, calculated on the starting racemic mixture.

10. Method as claimed in claim 4, wherein pyroglutamic acid in an optically active form is added in an amount of between 0.2 and 1.5 equivalent, calculated on the starting racemic mixture.

11. Method as claimed in claim 1, wherein the crystallization is performed in an alcoholic solvent.

12. Method as claimed in claim 2, wherein the crystallization is performed in an alcoholic solvent.

13. Method as claimed in claim 3, wherein the crystallization is performed in an alcoholic solvent.

14. Method as claimed in claim 4, wherein the crystallization is performed in an alcoholic solvent.

15. Method as claimed in claim 11, wherein the crystallization is performed in methanol, ethanol, isopropanol or n-butanol.

16. Method as claimed in claim 12, wherein the crystallization is performed in methanol, ethanol, isopropanol or n-butanol.

17. Method as claimed in claim 13, wherein the crystallization is performed in methanol, ethanol, isopropanol or n-butanol.

18. Method as claimed in claim 14, wherein the crystallization is performed in methanol, ethanol, isopropanol or n-butanol.

19. Method as claimed in any of claim 1, wherein the mother liquor or combined mother liquors, remaining after the separation of the crystallized acid addition salt, is (are) subjected to an after-treatment by successively (i) cleaving the dissolved acid addition salt to produce a solution of an enantiomers-mixture of imidazolyl compound of formula I, presented in claim 1, which mixture is reduced in the desired enantiomer, and (ii) by then converting said solution to a racemic mixture under the influence of a base.

20. Method as claimed in claim 19, wherein an inorganic base is used for the racemization.

21. Method as claimed in claim 20, wherein the inorganic base is an alkali metal hydroxide.

22. A crystalline hydrochloride monohydrate of compound of formula wherein:
n is 1;
m is 1;
$R_1$ is methyl; and
wherein said hydrochloride monohydrate of compound of formula (I) shows the following spectroscopic data:
(a) Infrared (=IR) spectra bands recorded in attenuated total reflectance (=ATR; spectral resolution 2 $cm^{-1}$, deuterated triglycine sulfate detector) in $cm^{-1}$ each band with a tolerance of ±2 $cm^{-1}$): 3461, 3405, 2103, 1729, 1649, 1628, 1606, 1460, 1281, 962;
(b) Powder X-ray diffraction (=XRD) angles (2 theta) measured on a diffractometer using monochromatic CuKα radiation, tube voltage 40 kV, tube current 40 mA: 5.7°±0.1°, 10.8°±0.1°, 11.4°±0.1°, 12.4°±0.1°, 17.2±0.1°, 22.7±0.1°, 23.0±0.1°, 24.5±0.1°, 27.4±0.1°, 35.0±0.1°.

23. A crystalline hydrochloride monohydrate of compound of formula (I) as claimed in claim 22, wherein said hydrochloride monohydrate of compound of formula (I) is further characterized by the Infrared (=IR) spectra essentially corresponding to that of FIG. 1.

24. A crystalline hydrochloride monohydrate of compound of formula (I) as claimed in claim 22, wherein said hydrochloride monohydrate of compound of formula (I) is further characterized by the Powder X-ray diffraction (=XRD) patterns essentially corresponding to that of FIG. 2.

* * * * *

UNITED STATES PATENT AND TRADEMARK OFFICE
CERTIFICATE OF CORRECTION

PATENT NO. : 6,365,743 B1
DATED : April 2, 2002
INVENTOR(S) : Paulus F.C. van der Meij et al.

It is certified that error appears in the above-identified patent and that said Letters Patent is hereby corrected as shown below:

Column 9,
The ninth acid appearing in the table should read as follows:

-- 2,3:4,6-Di-O-isopropylidene-2-keto-L-gulonic acid --

Column 10,
The formula appearing in claim 1 should read as follows:

Column 11,
The formula appearing in claim 2 should read as follows:

Signed and Sealed this

Twenty-fifth Day of March, 2003

JAMES E. ROGAN
*Director of the United States Patent and Trademark Office*